United States Patent [19]

Hosoi et al.

[11] 4,250,169

[45] Feb. 10, 1981

[54] METHOD OF PRODUCING ANTIBIOTICS SUPPOSITORIES

[75] Inventors: Kaoru Hosoi; Tadamasa Ikeda, both of Yokohama; Takemi Nakayoshi, Kawasaki; Akira Okada, Zushi, all of Japan

[73] Assignee: Meiji Seika Kaisha Ltd., Japan

[21] Appl. No.: 45,967

[22] Filed: Jun. 6, 1979

Related U.S. Application Data

[63] Continuation of Ser. No. 870,524, Jan. 18, 1978, abandoned.

[30] Foreign Application Priority Data

Jan. 21, 1977 [JP] Japan .................................. 52-4854

[51] Int. Cl.$^3$ ...................... A61K 31/70; A61K 31/71
[52] U.S. Cl. .................................... 424/181; 424/180;
424/DIG. 15
[58] Field of Search ................ 424/180, 181, DIG. 15

[56] References Cited

U.S. PATENT DOCUMENTS

| | | | |
|---|---|---|---|
| 2,854,378 | 9/1958 | Buckwalter | 424/271 |
| 2,931,798 | 4/1960 | Umezawa et al. | 424/181 |
| 2,975,099 | 3/1961 | Goyan et al. | 424/181 |
| 3,325,472 | 6/1967 | Sackler | 424/227 |

FOREIGN PATENT DOCUMENTS 1915191  10/1969  Fed. Rep. of Germany ........... 424/114

OTHER PUBLICATIONS

The Merck Index, 9th Ed. (1976). #2969.

*Primary Examiner*—allen J. Robinson
*Attorney, Agent, or Firm*—John J. McGlew

[57] ABSTRACT

A method of producing aminoglycoside antibiotics in the form of suppositories which comprises dispersing an aminoglycoside antibiotic substance or its non-toxic salts in an oleaginous or aqueous base to which at least a nonionic surface-active agent and/or an anionic surface active agent are added and forming said substances with said base into a pharmaceutically safe and effective suppository for using in living animals and humans, e.g. in infants.

1 Claim, No Drawings

METHOD OF PRODUCING ANTIBIOTICS SUPPOSITORIES

This is a continuation of application Ser. No. 870,524 filed Jan. 18, 1978 and now abandoned.

BACKGROUND OF THE INVENTION

The present invention relates to a method of producing aminoglycoside antibiotics suppositories.

The systemic administration of medicine is usually performed either orally or by injection. Aminoglycoside antibiotics, when administered orally, are very poorly absorbed through digestive tracts and as a result the concentration thereof in the blood cannot reach an effective therapeutic level. Therefore, these antibiotics are administered only by injection at present. Incidentally, the capsules and granules of these antibiotics whch are now on sale as medicines for oral administration are intended not to be absorbed through digestive tracts but to control bacterial infections inside the digestive tracts.

Aminoglycoside antibiotics, including streptomycin, kanamycin, bekanamycin, ribostamycin, gentamycin, amikacin, tobramycin, dibekacin and others, consist of a group of antibiotics which are substances very effective in the treatment of bacterial infections, since they act extensively on Gram-positive bacteria, Gram-negative bacteria, acid-fast bacteria, etc. At present, however, the systemic administration of these antibiotics is necessarily performed by injection, especially by intramuscular injection for the reasons mentioned above. Thus, it has been heretofore considered totally impossible to achieve the effective absorption of such aminoglycoside antibiotics by any of the usual administration methods except for injection. Also, there has been no report known to the present inventors as yet on a procedure by which these aminoglycoside antibiotics were successfully absorbed in the body by any of the usual methods except for injection.

Recently, however, it was revealed that intramuscular injection especially for infants might cause muscular atrophy. Since then, it has been eagerly desired to establish a safe systemic administration method especially for infants, instead of injection.

SUMMARY AND OBJECTS OF THE INVENTION

It is, therefore, an object of the present invention to provide a method of producing aminoglycoside antibiotics in the form of suppositories which make it possible to achieve the effective absorption of aminoglycoside antibiotics without relying upon the disadvantageous administration methods as have been mentioned above.

Suppositories for systemic administration have the following advantages, as is well known, and, therefore, are very useful: they require no medical assistance when administered, as in the case of injections; they can be easily administered even in case of emergency at night; they give no pain or local disturbance when administered; they can be administered safely and easily even to infants; they undergo no drug inactivation action by gastric juices, unlike oral drugs, and they exert no irritant action on gastrointestinal tracts; they can be administered to patients to whom oral administration is impossible; and they have other useful features. The inventors of the present invention made efforts for many years to realize the effective rectal absorption of aminoglycoside antibiotics prepared in the form of suppositories. More particularly, the inventors of the present invention dispersed an aminoglycoside antibiotic substance or its salt in an oily or aqueous base mixed with at least a nonionic surface-active agent and/or anionic surface-active agent, and thereby enabled the rectal absorption of the antibiotic and succeeded in achieving the effective blood concentration thereof. In this case, the dosage may be made in form of suppositories specified in the Japanese Pharmacopoeia or in the form of a paste. In the latter case, the paste-like medicine is injected into the rectum.

DESCRIPTION OF SPECIFIC EMBODIMENT OF THE INVENTION

According to the present invention, there is provided a method of producing aminoglycoside antibiotic suppositories which comprises dispersing an aminoglycoside antibiotic substance or a non-toxic salt thereof in an oily or aqueous base to which at least a nonionic surface-active agent and/or an anionic surface-active agent are added, and forming said substance with said bore into a pharmaceutically acceptable antibiotic suppository.

The aminoglycoside antibiotics that can be used in the present invention include streptomycin, kanamycin, bekanamycin, ribostamycin, gentamycin, amikacin, tobramycin, dibekacin, etc., and their sulfates, hydrochlorides and other non-toxic salts which can maintain inherent "basic" properties when dissolved into solutions.

The oily or oleaginous bases used in the present invention include those usually used for producing suppositories: for instance, oils and fats such as sesame oil, olive oil, soybean oil, cacao butter, coconut oil, beef tallow and lard; those obtained by modifying the above-mentioned oils and fats through hydrogenation, fatty acid exchange or by other processes; mineral oils such as vaseline and paraffin; and higher fatty acids such as stearic acid and oleic acid. These oils, fats, mineral oils and fatty acids may be used singly or in combination.

The aqueous bases that can be used in the present invention include polyoxyethylene glycol, propylene glycol, glycerogelatin, etc., which may be used singly or in combination.

As the nonionic surface-active agent in the present invention the following agents are useful, for instance, polyoxyethylene nonylphenyl ether (for instance, "EMULGEN-903" and "EMULGEN-920" produced by KAO ATRAS CO., LTD., and "NIKKOL NP-10" produced by NIKKO CHEMICALS CO., LTD.), polyoxyethylene alkyl ether (for instance, "Lauromacrogol" listed in the Pharmacopoeia, and "NIKKOL BC-20" produced by NIKKO CHEMICALS CO., LTD.), polyoxyethylene sorbitan fatty acid ester (for instance, "Polysorbate 80" listed in the Pharmacopoeia, and "NIKKOL TO-10" produced by NIKKO CHEMICALS CO., LTD.), and polyoxyethylene stearate (for instance, "Polyoxyl 40 stearate" listed in the Pharmacopoeia, and "NIKKOL MYS-40" produced by NIKKO CHEMICALS CO., LTD.).

As the anionic surface active agent in the present invention the following agents are useful for instance, sodium lauryl sulfate (for instance, "NIKKOL SLS" produced by NIKKO CHEMICALS CO. LTD.), sodium lauryl phosphate (for instance, "NIKKOL SLP-N" produced by NIKKO CHEMICALS, CO., LTD.), and alkyl-sulfo-succinate (for instance, "AEROSOL OT" produced by ACC CO., LTD., and "NIKKOL OTP-100" produced by NIKKO CHEMICALS CO., LTD.)

The addition of the surface-active agent is preferably in the range of about about 2 to 10% by weight of the suppository.

Although the addition of the above-mentioned antibiotic substance is variable according to the desired therapeutic doses, it is generally 5 to 80% by weight. The above-mentioned oleaginous or aqueous base can be used in a desired amount to form suppositories Now the present invention will be hereinafter described in detail with reference to several examples:

EXAMPLE 1

10 g (in potency) of bekanamycin was added to a mixture containing 10 g of polyoxyethylene stearate ("NIKKOL MYS-25" produced by NIKKO CHEMICALS CO., LTD.) and 80 g of an oleaginous base called "WITEPSOL H-15" (glycerin trifatty acid ester, produced by DYNAMITE NOBEL CO., LTD.), and was fully dispersed therein while being heated at 60° C. The product thus obtained was poured into individual suppository containers, 1.5 g for each; then the resultant mixture was naturally cooled to obtain the desired suppositories. One of these suppositories was rectally administered to a rabbit (about 3 kg in weight). Blood samples were collected when the following specified periods of time had elapsed after administration, and the concentration of bekanamycin in the blood was measured in the usual manner. Bekanamycin suppositories containing no polyoxyethylene stearate were similarly produced as a control; in this case, the bekanamycin suppositories were hardly absorbed, and as a result, the concentration of bekanamycin in the blood was only 1 to 5 μg (in potency)/ml. On the other hand, the bekanamycin suppositories produced in the above-mentioned manner according to the present invention were absorbed very well as shown in Table 1 given below.

TABLE 1

| Blood-sample collection time (hours after administration) | 1 hour | 2 hours | 4 hours | 8 hours |
| --- | --- | --- | --- | --- |
| Blood level of bekanamycin (μg(in potency)/ml) According to present invention | 48.0 | 32.8 | 20.1 | 3.5 |
| According to prior art | Essentially nil | Essentially nil | Essentially nil | Essentially nil |

EXAMPLE 2

Bekanamycin sulfate suppositories were produced in the same way as in the case of Example 1. Absorption tests obtained almost the same results as above as shown in Table 2.

TABLE 2

| Blood-sample collection time (hours after administration) | 1 hour | 2 hours | 4 hours | 8 hours |
| --- | --- | --- | --- | --- |
| Blood level of bekanamycin (μg(in potency)/ml) According to prior art | 45.0 Essentially nil | 35.5 Essentially nil | 21.8 Essentially nil | 5.4 Essentially nil |

EXAMPLE 3

10 g (in potency) of bekanamycin sulfate was added to a mixture containing 10 g of polyoxyethlene stearate ("NIKKOL MYS-45" produced by NIKKO CHEMICALS CO., LTD.) and 80 g of an aqueous base called "Macrogol 6000" (polyethylene glycol, listed in the Pharmacopoeia), and was fully dispersed therein while being heated and mixed at 60° C. The product thus obtained was poured into individual suppository containers, 1.5 g for each; and then was naturally cooled to obtain desired suppositories. One of these suppositories was rectally administered to a rabbit (about 3 kg in weight); then, blood samples were collected when the following periods of time had elapsed after administration, and the concentration of bekanamycin in the blood or, in other words, the blood level of bekanamycin was measured in the usual manner. Absorption was very good as in the case of Example 1 as seen in Table 3 below.

TABLE 3

| Blood-sample collection time (hours after administration) | 1 hour | 2 hours | 4 hours | 8 hours |
| --- | --- | --- | --- | --- |
| Blood level of bekanamycin (μg(in potency)/ml) According to the present invention | 59.0 | 29.0 | 10.8 | 0.9 |

EXAMPLE 4

10 g (in potency) of ribostamycin sulfate or 10 g of streptomycin sulfate was added to a mixture containing 5 g of polyoxyethylene stearate ("NIKKOL MYS-45") and 85 g of cacao butter, and was fully dispersed therein while being heated and mixed; then the product thus obtained was processed into desired suppositories in the same manner as in the case of Example 1. The blood level of ribostamycin and that of streptomycin were also measured respectively. The results proved that absorption was very good as shown in the following Table 4

TABLE 4

| Blood-sample collection time (hours after administration) | 1 hour | 2 hours | 4 hours | 8 hours |
| --- | --- | --- | --- | --- |
| Blood level of ribostamycin (μg(in potency)/ml) According to the present invention | 40.0 | 41.2 | 20.9 | 3.0 |
| Blood level of streptomycin (μg(in potency)/ml) According to the present invention | 32.8 | 29.5 | 19.8 | 5.0 |

EXAMPLE 5

5 g (in potency) of bekanamycin sulfate was added to 2.3 g of "WITEPSOL W-35" (glycerin trifatty acid ester, produced by DYNAMITE NOBEL CO., LTD.). To this mixture obtained in this manner, 2 g of each of the following surface-active agents was added independently in order to obtain different specimens. Each specimen was heated at 60° C. and mixed for dispersion of bekanamycin sulfate, and then was poured into individual suppository containers, 0.9 g for each, and then was naturally cooled to obtain the desired suppositories. One of these suppositories was rectally administered to a rabbit (about 3 kg in weight). Then, blood samples were collected at each measuring time specified below in Table 5, and the blood level at that time was measured. As shown in the following table, the absorption of the suppositories thus produced was far better than that of the reference suppositories with no surface-active agent.

TABLE 5

| Kinds of surface active agent | Blood-sample collection time (Unit: μg(in potency)/ml) | | | |
|---|---|---|---|---|
| | 1 hour | 2 hours | 4 hours | 8 hours |
| Control (Prior Art) | 2.5 | 1.5 | trace | 0 |
| NIKKOL MYS-45(polyoxy-ethylene stearate) (Present Invention) | 28.9 | 20.8 | 7.0 | trace |
| NIKKOL TO-10(polyoxy-ethylene sorbitan fatty acid ester) (Present Invention) | 18.0 | 11.4 | 6.6 | 1.7 |
| NIKKOL SLS(sodium lauryl sulfate) (Present Invention) | 21.2 | 13.3 | 5.8 | trace |
| NIKKOL OTP-100(alkyl-sulfo-succinate) (Present Invention) | 18.9 | 12.2 | 4.9 | 0.8 |

EXAMPLE 6

To 50 g of "WITEPSOL W-35" (produced by DYNAMITE NOBEL CO., LTD.) 1 g (in potency) of dibekacin sulfate was added. To the mixture thus obtained, 2.5 g of each of the following surface-active agents was added independently in order to obtain different specimen. Each specimen was heated at 60° C. and mixed to obtain a dispersion of dibekacin sulfate, and then was poured into individual suppository containers, 0.8 g for each, after which each was naturally cooled to obtain the desired suppositories. One of these suppositories was rectally administered to a rabbit (about 3 kg in weight). Then, blood samples were collected at every measuring time given below in Table 6, and the blood level at that time was measured. As shown in the following Table 6, the blood level was very good.

TABLE 6

| Kinds of surface active agents | Blood-sample collection time (Unit: μg(in potency)/ml) | | | |
|---|---|---|---|---|
| | 1 hour | 2 hours | 4 hours | 8 hours |
| NIKKOL BC-20TX(polyoxy-ethylene (20) cetyl ether) (Present Invention) | 24.5 | 22.9 | 8.8 | 1.8 |
| NIKKOL BL-9(polyoxy-ethylene lauryl ether) (Present Invention) | 20.0 | 17.2 | 8.5 | 2.3 |

EXAMPLE 7

1.5 g (in potency) of dibekacin sulfate, 94 g of "WITEPSOL W-35" (DYNAMITE NOBEL CO., LTD.), and 4.2 g of polyoxyethylene cetyl ether were mixed and melted. The mixture thus obtained was poured into individual suppository containers, 3 g for each, and then was naturally cooled to obtain the desired suppositories. One of these suppositories was rectally administered to a dog (about 10 kg in weight). Blood samples were collected at every measuring time given below in Table 7, and the blood level was measured at that time. As a result, it was found that the effective blood level in the case of this specimen was far better than that in the case of the reference specimen similarly produced but containing no polyoxyethylene cetyl ether.

TABLE 7

| Kinds of specimens | Blood-sample collection time (Unit: μg (in potency)/ml) | | | | | | |
|---|---|---|---|---|---|---|---|
| | 0.25 hr | 0.5 hr | 1 hr | 2 hrs | 4 hrs | 6 hrs | 8 hrs |
| Control (Prior Art) | 0 | tr. | tr. | 0 | 0 | 0 | 0 |
| Specimen with surfactant according to the invention (Present Invention) | 1.8 | 5.7 | 4.5 | 2.4 | 1.2 | 0.3 | 0 |

EXAMPLE 8

5 g (in potency) of bekanamycin sulfate, 3.6 g of an aqueous base called "Macrogol 1500" (polyethylene glycol, listed in the Pharmacopoeia), 10.9 g of polyoxyethylene stearate ("NIKKOL MYS-45" produced by NIKKO CHEMICALS CO., LTD.) and sodium lauryl phosphate ("NIKKOL SLP-N" produced by NIKKO CHEMICALS CO., LTD.) were mixed and melted (at about 60° C.). The mixture thus obtained was poured into individual suppository containers, 1 g for each, and then was naturally cooled to obtain desired suppositories. One of these suppositories was rectally administered to a rabbit (about 3 kg in weight). Then, blood samples were collected when the following periods of time had elapsed after administration, and the blood level of bekanamycin was measured in a usual manner. The effective blood level was found as shown in the following Table 8.

TABLE 9

| Blood-sample collection time | 0.5 hour | 1 hour | 2 hours | 4 hours |
|---|---|---|---|---|
| Blood level (μg(in potency)/ml) According to the present invention | 50.9 | 53.2 | 54.3 | 20.1 |

What is claimed is:

1. A suppository for the therapeutic administration of dibekacin comprising, a mixture of about 10% by weight of dibekacin sulfate with glycerin trifatty acid ester and from 2 to 10% by weight of the surface active agent polyoxyethylene (20) cetyl ether, the remaining percentage by weight being the glycerin trifatty acid ester.

* * * * *